US012150749B2

(12) United States Patent
Coppens et al.

(10) Patent No.: US 12,150,749 B2
(45) Date of Patent: Nov. 26, 2024

(54) ACCESSORY KIT FOR INTERVENTIONAL PROCEDURES USING MAGNETIC RESONANCE IMAGING

(71) Applicants: Qfix Systems, LLC, Avondale, PA (US); Otto-von Guericke Universität Magdeburg, Magdeburg (DE); Medizinische Hochschule Hannover, Hannover (DE)

(72) Inventors: Daniel D. Coppens, Avondale, PA (US); Enrico Pannicke, Magdeburg (DE); Oliver Speck, Magdeburg (DE); Frank Wacker, Hannover (DE); Bennet Hensen, Hannover (DE)

( * ) Notice: Subject to any disclaimer, the term of this patent is extended or adjusted under 35 U.S.C. 154(b) by 252 days.

(21) Appl. No.: 17/781,635

(22) PCT Filed: Dec. 1, 2020

(86) PCT No.: PCT/US2020/062746
§ 371 (c)(1),
(2) Date: Jun. 1, 2022

(87) PCT Pub. No.: WO2021/113262
PCT Pub. Date: Jun. 10, 2021

(65) Prior Publication Data
US 2023/0000382 A1    Jan. 5, 2023

Related U.S. Application Data

(60) Provisional application No. 62/942,451, filed on Dec. 2, 2019.

(51) Int. Cl.
*A61B 5/055*    (2006.01)
*A61B 5/00*    (2006.01)
(Continued)

(52) U.S. Cl.
CPC .............. *A61B 5/055* (2013.01); *A61B 5/704* (2013.01); *A61B 6/0442* (2013.01); *H01R 31/06* (2013.01)

(58) Field of Classification Search
None
See application file for complete search history.

(56) References Cited

U.S. PATENT DOCUMENTS

| 6,446,286 | B1 | 9/2002 | Karmalawy |
| 6,832,399 | B2 | 12/2004 | Falbo et al. |

(Continued)

FOREIGN PATENT DOCUMENTS

CA    2661674 C  *  12/2012  .......... A61B 5/0555

OTHER PUBLICATIONS

International Preliminary Report on Patentability and Written Opinion for International Application No. PCT/US2020/062746, issued May 17, 2022, 15 pages.

(Continued)

*Primary Examiner* — Tho D Ta

(57) ABSTRACT

An accessory kit is provided for interventional procedures using a magnetic resonance imaging scanner. The accessory kit includes a patient support and an electrical connection adapter. The patient support has a first end proximal and a second end distal to the scanner. The distal end is configured to create a space to accommodate a clinician, such as narrowing of the distal end or at least one cutout on a side of the distal end. The electrical connection adapter interfaces with the scanner and a scanner table. The accessory kit is configured so that when the proximal end is extended into the scanner bore, the distal end extends outside the bore. The narrowed width and/or cutout(s) of the exposed distal end and the extended gap between the scanner and scanner table (Continued)

create space on at least one side of the patient support that a clinician may use to access a patient.

13 Claims, 12 Drawing Sheets

(51) Int. Cl.
    *A61B 6/04*     (2006.01)
    *H01R 31/06*     (2006.01)

(56) References Cited

U.S. PATENT DOCUMENTS

| 2013/0184564 A1 | 7/2013 | Ninomiya et al. |
| 2014/0296692 A1 | 10/2014 | Iizuka et al. |
| 2017/0311802 A1 | 11/2017 | Bollenbeck et al. |

OTHER PUBLICATIONS

International Search Report and Written Opinion for International Application No. PCT/US2020/062746, dated May 17, 2021, 19 pages.

\* cited by examiner

ACCESSORY KIT FOR INTERVENTIONAL PROCEDURES USING MAGNETIC RESONANCE IMAGING

CROSS-REFERENCE TO RELATED APPLICATIONS

This is the U.S. National Phase Application of International Application No. PCT/US2020/062746, filed Dec. 1, 2020, which claims priority to U.S. Provisional Application No. 62/942,451, filed on Dec. 2, 2019, the contents of each of which are incorporated by reference herein in their entireties, for all purposes.

FIELD OF THE INVENTION

The present invention is directed to an accessory kit for interventional procedures using magnetic resonance imaging and methods of employing the same.

SUMMARY OF THE INVENTION

The present invention is directed to an accessory kit for interventional procedures in magnetic resonance imaging (MRI) environments. The accessory kit is designed to enable enhanced ability to perform interventional procedures in a magnetic resonance environment by providing improved ergonomic characteristics and improved electronic access to MR machine data, power, and ports. The accessory kit is used with an existing MR scanner to provide the enhanced capability.

The accessory kit comprises a patient support and an electrical connection adapter which work in tandem to achieve the stated design objectives. The patient support is configured to attach to or replace the existing surface of the MR scanner table and to fit within the bore of the MR scanner. The patient support comprises a first end, proximal to the scanner bore, and a second end, distal to the scanner bore and coupled to the scanner table. Provision is made at the distal end of the patient support to accommodate the clinician. The electrical connection adapter is configured to connect the MRI scanner to the MRI table while creating a gap between the two such that it creates space for the clinician to stand or kneel to access the patient.

When installed with a compatible MR scanner, the accessory kit is configured in such a way that, when the proximal end of the patient support is fully extended into the bore of the MR scanner, the distal end portion of the patient support is exposed outside the bore over the extended gap created by the electrical connection adapter. At this point in operation, the exposed distal end portion and the additional distance between the scanner and table create spaces on one or both sides of the patient support that a clinician may step into, or otherwise at least partially enter, in order to access the patient during the scan to perform necessary clinical tasks.

DETAILED DESCRIPTION OF THE INVENTION

Figure 1A:
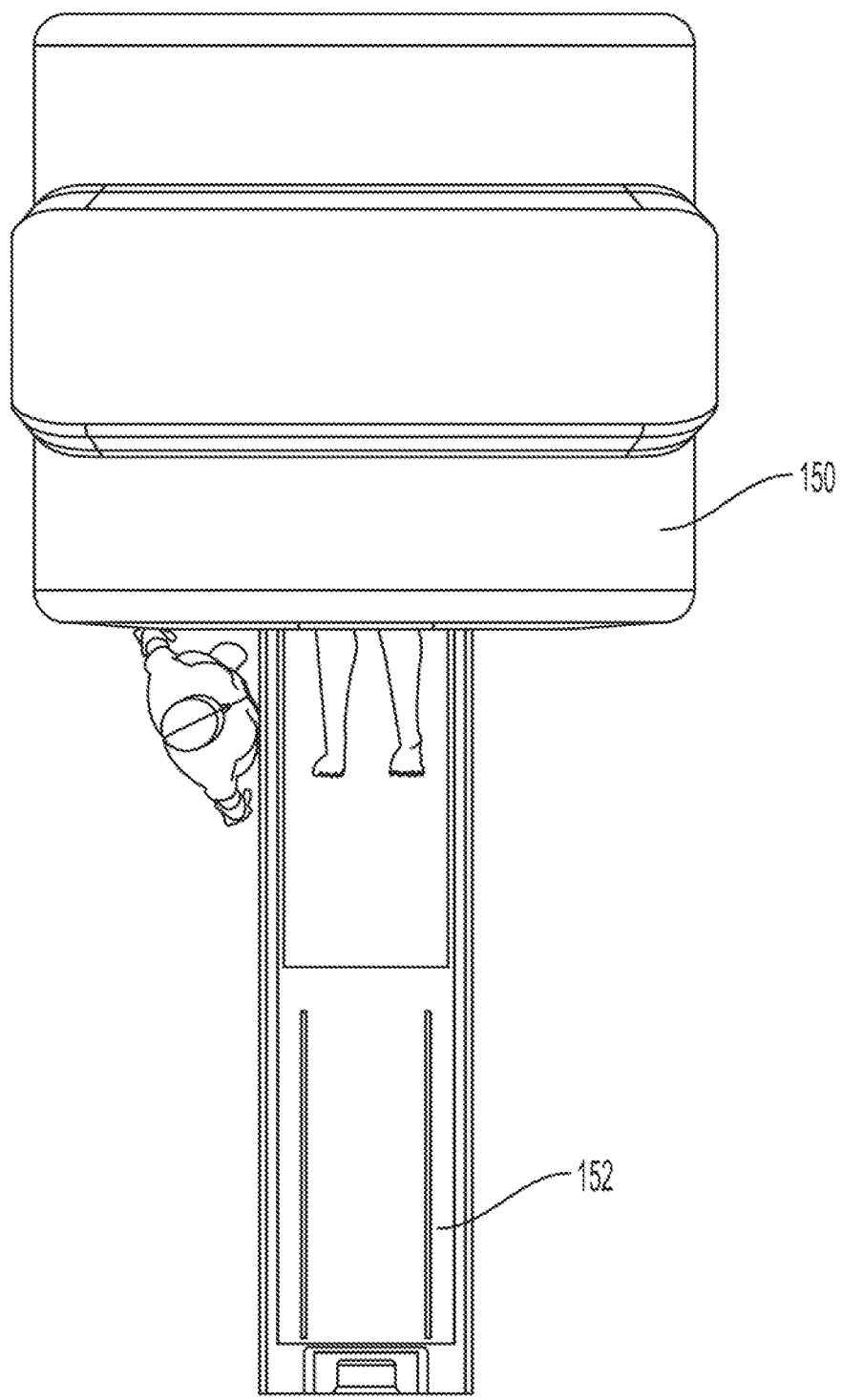
FIGS. 1A-C are top, perspective, and cross-sectional views of an exemplary scanner and table system.
Figure 1B:
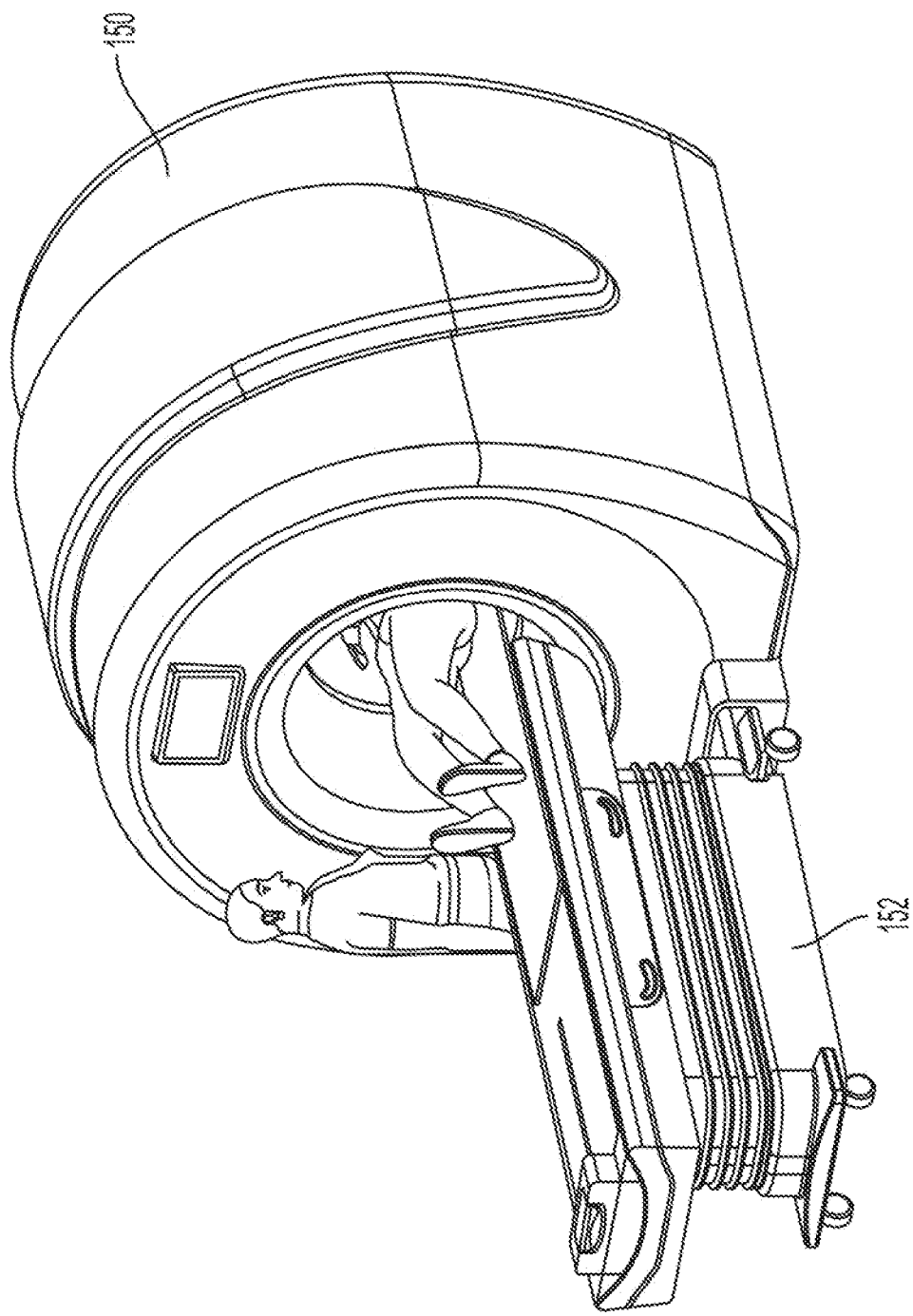
Figure 1C:
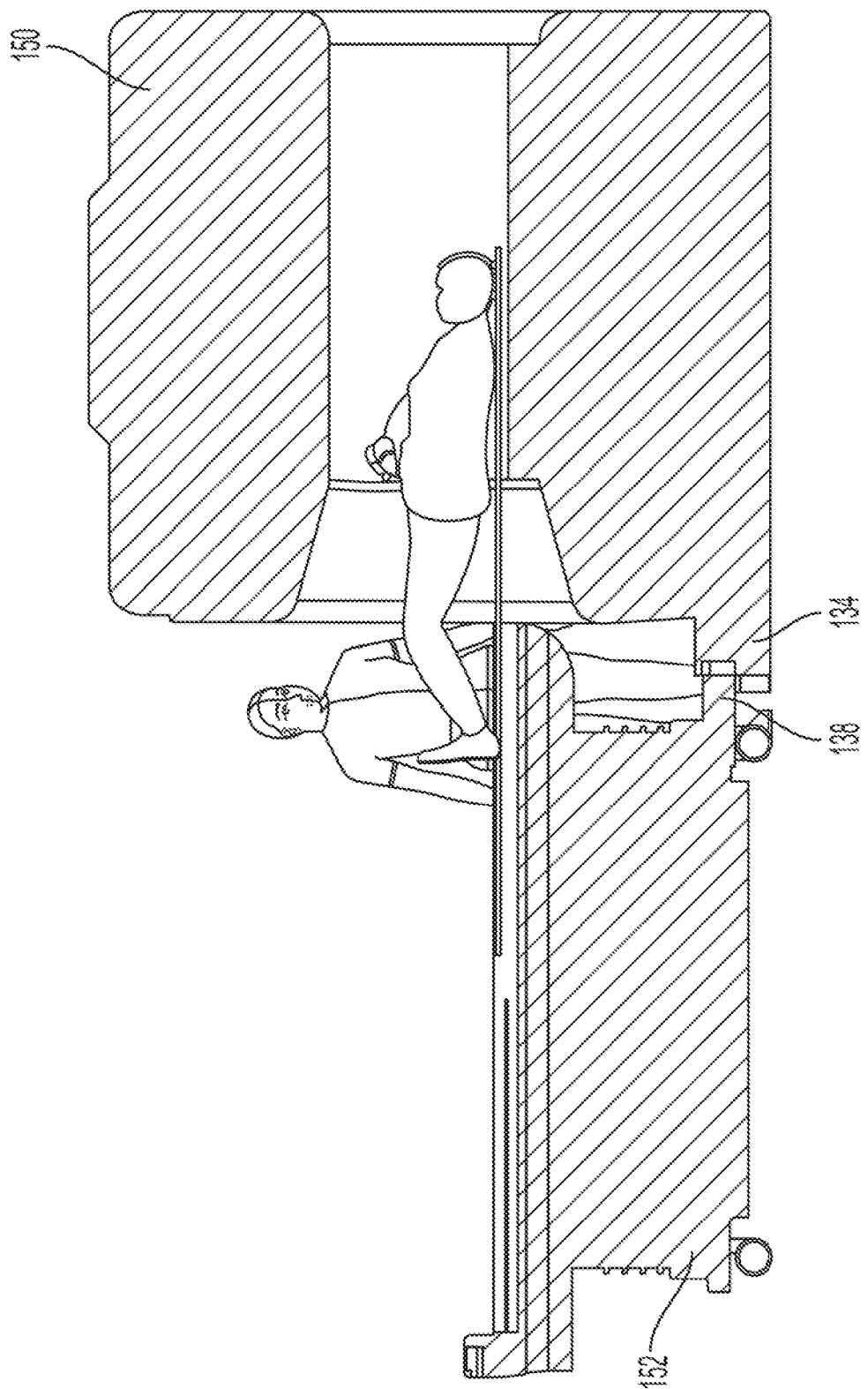

Magnetic resonance imaging (MRI) is used in various, broad-ranging interventional applications, such as in the treatment of stroke and other neurological dysfunctions, various cardiovascular interventions, MR-guided biopsy, MR-guided injections, low dose rate (LDR) brachytherapy seed implantation, MR-guided ultrasound therapy, and MR-guided ablations (using, for example, ultrasound, radiofrequency, or microwave devices). Existing magnetic resonance systems pose various challenges for clinicians intending to use MRI for interventional radiology. Access to the patient while the patient is positioned in the bore of the MR scanner is typically restricted by the geometry of both the table of the MR scanner on which the patient is positioned and the electronic interfaces intended to dock removable tables to the scanner.

For example, such electronic interfaces of exemplary MR scanners are commonly located at floor level at the front of the scanner bore. The patient table contains a mating electrical connector allowing for the transmission of power and data, including signals from integrated coils located underneath the patient support of the table. As a result of the table geometry and electrical connection, the clinician may be forced to lean across the table to access the patient in the bore. In addition, as the desire for high quality images and higher strength magnets has risen, the length of the bore has increased. This means the patient is positioned comparatively deeper into the bore of the MR scanner, requiring the clinician to move even deeper into the bore to accomplish interventional procedures. Depending on the bore geometry and physical size of the clinician, it may not even be possible for the clinician to carry out his or her task.

Aside from being ergonomically awkward, this can pose risks to the clinician and patient, such as the entanglement in intravenous medication tubing (and subsequent inadvertent disruption of delivery of such medication), compression of vital structures of the patient, and hampering of the clinician's ability to perform both the procedure required as well as any emergency interventions that may be needed. Additionally, due to the singular nature of the electronic connection between the table and the scanner, access to the data from the MR machine or the associated integrated coils can also be restricted, limiting the ability to link in to monitors, data capture machines, or other equipment that would help the clinician better visualize the area of interest in real time.

There are several aspects to the current invention: an accessory kit for use with an MR scanner and MR scanner table for use during interventional procedures, a method of appropriately utilizing the accessory kit, an MR Imaging system for access during interventional procedures, and a method of configuring an MR imaging system for access during interventional procedures.

In accordance with a first aspect of the invention, an accessory kit 100 is provided for use with an MR scanner 150 and an MR scanner table 152 during interventional procedures using magnetic resonance imaging. The accessory kit 100 includes a patient support 110 configured to be positioned on the MR scanner table 152 and having a surface extending between a proximal end 114 and a distal end 112, wherein at least one recess 116 is defined in the patient support 110 and extends inwardly from a perimeter of the patient support 110 toward a central region of the patient support 110, the at least one recess 116 being positioned at a distal end portion of the patient support 110 and adapted to at least partially receive a medical professional during interventional procedures. The accessory kit 100 also includes an electrical connection adapter 130 configured to be interposed between the MR scanner 150 and the MR scanner table 152, thereby creating or extending a gap 142 between the MR scanner 150 and the MR scanner table 152 when the electrical connection adapter 130 is interposed between the MR scanner 150 and the MR scanner table 152. The electrical connection adapter 130 has an external enclosure 140; a proximal connector 132 positioned at a proximal end of the external enclosure 140, the proximal connector 132 being configured to electrically couple the electrical connection adapter to a connector 134 of the MR scanner 150; and a distal connector 136 positioned at a distal end of the external enclosure 140, the distal connector 136 being configured to electrically couple the electrical connection adapter 130 to a connector 138 of the MR scanner table 152.

The at least one recess 116 of the accessory kit 100 can include at least one cutout 118 in at least one side of the patient support 110. Also, the patient support 110 can include a structural spine 122, wherein the structural spine 122 runs at least a portion of the length of the patient support 110 and has a thickness no less than the thickness of a proximal end portion of the patient support at the proximal end 112 of the patient support. The thickness of the structural spine 122 can increase in a longitudinal direction extending from the proximal end 112 to the distal end 114 of the patient support 110. The at least one recess 116 can extend to the distal end 114 of the patient support 110 such that a width of the patient support 110 at the distal end 114 is narrower than a width of the patient support 110 at the proximal end 112. The width of the distal end 112 of the patient support can be selected to be no greater than 10 cm. The patient support 110 can replace a surface of a conventional MR scanner table 152. The patient support 110 can also include at least one filler plate 120 positionable to fill in the at least one recess 116. The patient support 110 is preferably composed only of materials which are compatible with magnetic resonance imaging environments, and the patient support can be composed of non-ferromagnetic, non-conducting, and non-metallic composite materials.

The patient support 110 can include indicia configured to aid in alignment of a region of interest to an isocenter of the MR scanner. Also, the length of the gap 142 created or extended by the electrical connection adapter 130 is between 0.25 m and 1 m. The electrical connection adapter 130 can also include additional ports 144 for supplemental power and data output, the enclosure 140 of the electrical connection adapter 130 can be configured and positionable to permit a medical professional to kneel on its top 141 it, and the enclosure 140 of the electrical connection adapter 130 can also include ergonomic surfaces configured for enhancing comfort of the medical professional.

The gap 142 created or extended by the electrical connection adapter 130 and the at least one recess 116 are longitudinally co-located. For example, they can be co-located when the patient support 110 is positioned on the MR scanner table 152, the electrical connection adapter 130 is interposed between the MR scanner 150 and the MR scanner table 152, and the patient support 110 is moved relative to the MR scanner table 152 towards a bore of the MR scanner 150 and the proximal end 112 of the patient support 110 extends into the bore of the MR scanner 150.

Referring specifically to embodiments selected for illustration purposes, the accessory kit 100 comprises a patient support 110 and an electrical connection adapter 130. In a preferred embodiment, the patient support 110 is configured to attach to the existing surface of the MR scanner table 152 and to fit within the bore of the MR scanner 150. In another embodiment, the patient support 110 may instead replace the existing surface of the MR scanner table 152.

In a preferred embodiment, the patient support is comprised of composite materials which are compatible with the magnetic resonance environment (e.g. materials which are non-conducting, non-ferromagnetic, and non-metallic). The patient support 110, like existing table tops, may further comprise integrated MR coils or electrical connections intended to attach to MR coils. In a preferred embodiment, the patient support 110 may further comprise crosshairs or other surface markings at the point at which the isocenter of the MR scanner 150 will be located when the patient support 110 is fully extended into the bore of scanner 150. This allows enhanced alignment of the area of interest of the patient during the interventional procedure.

Figure 2A:
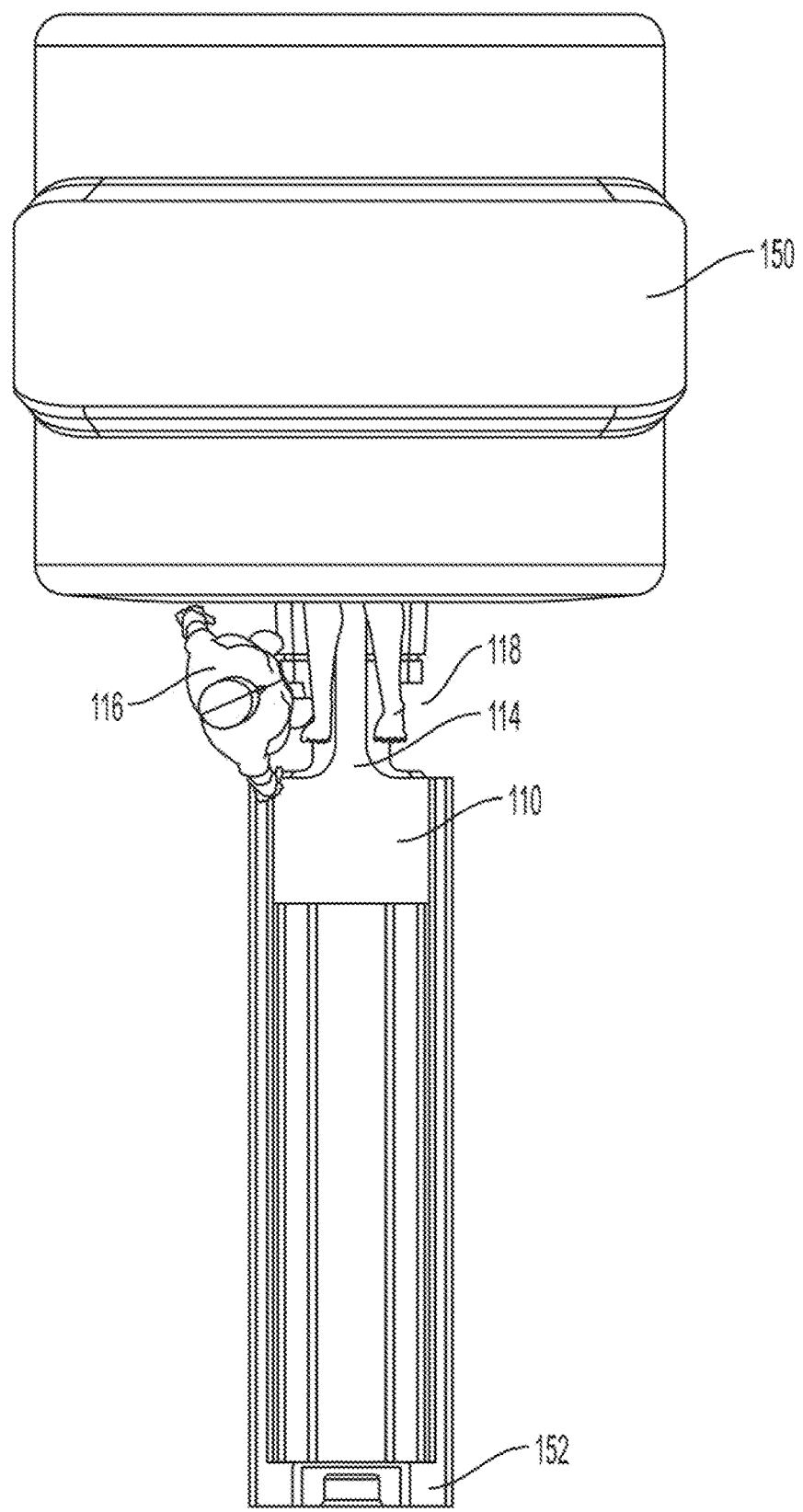
FIGS. 2A and B are top and perspective views of a first embodiment of the accessory kit of the present invention installed on an MR scanner.
Figure 3A:
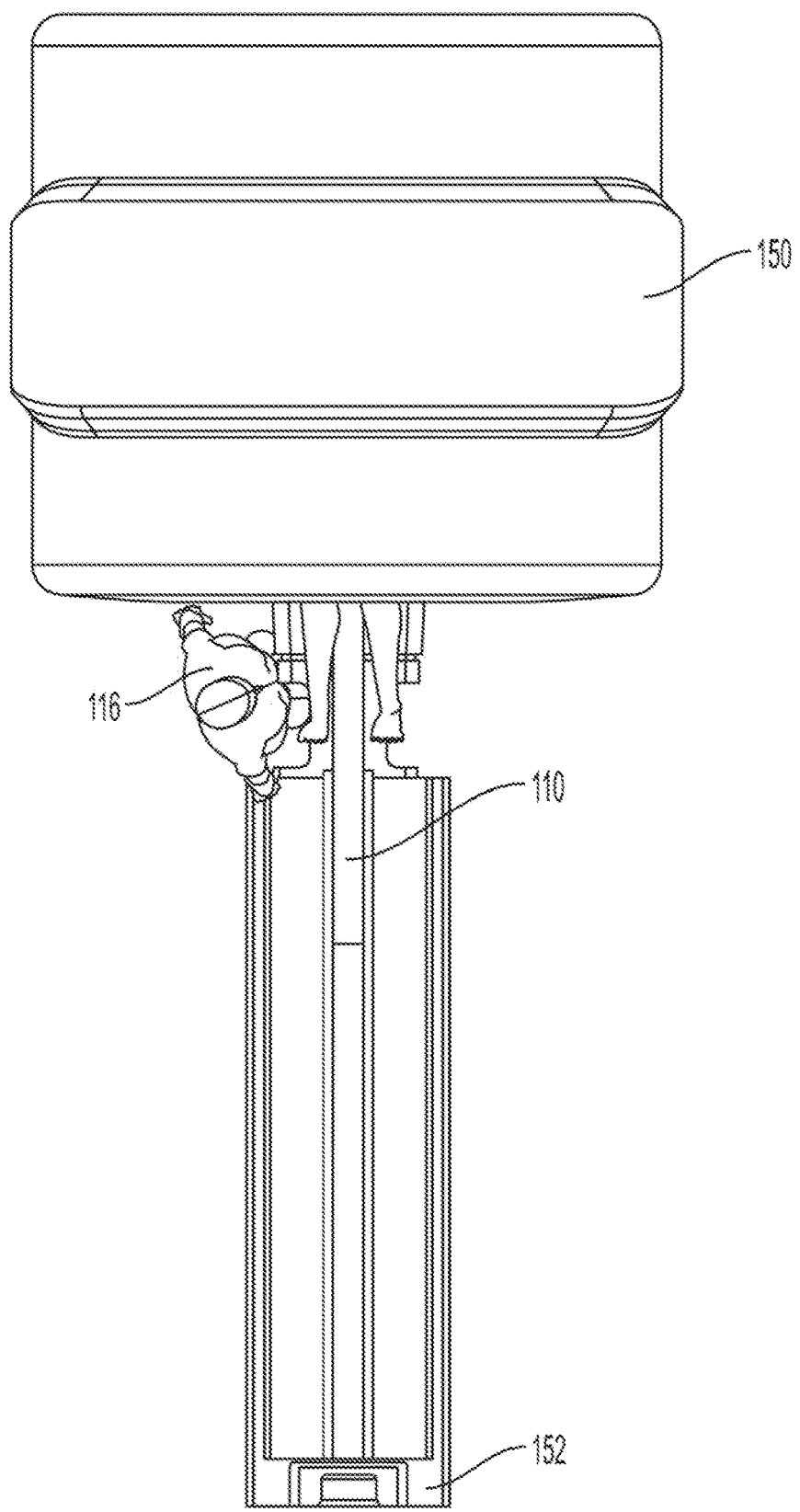
FIGS. 3A and B are top and perspective views of a second embodiment of the accessory kit of the present invention installed on an MR scanner.
Figure 3B:
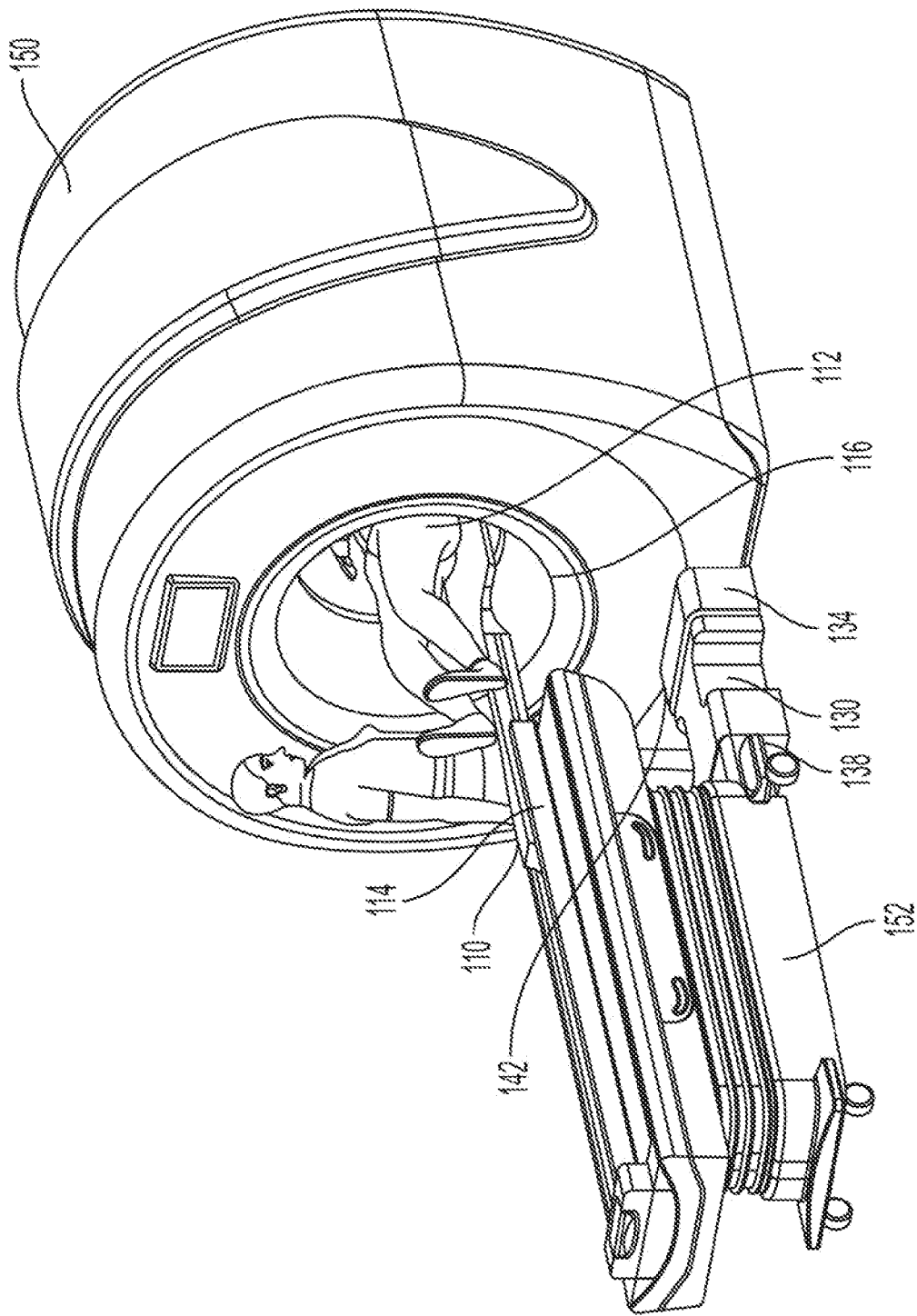

The patient support 110 has a first end, proximal to the scanner bore (the proximal end 112) and a second end, distal to the scanner bore (the distal end 114) and attached to the scanner table 152. Provision is made at the distal end 114 of the patient support 110 to create at least one recess 116 to at least partially receive the body of a clinician. In one embodiment, this can take the form of at least one cut out 118 on either or both sides of the patient support 110, as shown in FIGS. 2A and B and FIG. 5 B. In another preferred embodiment, this can be achieved by narrowing the patient support at the distal end 114, as shown in FIGS. 3A and B and FIG. 6 B.

When the patient support is extended into the bore of the scanner 150, the at least one recess 116 created by the distal end 114 of the patient support 110 is positioned just outside of the entrance of the bore of the MR scanner. This allows the clinician to place at least part of his or her body in each such recess 116 as well as the gap extending between the bore of the MR scanner and the MR scanner table 152.

Figure 5A:
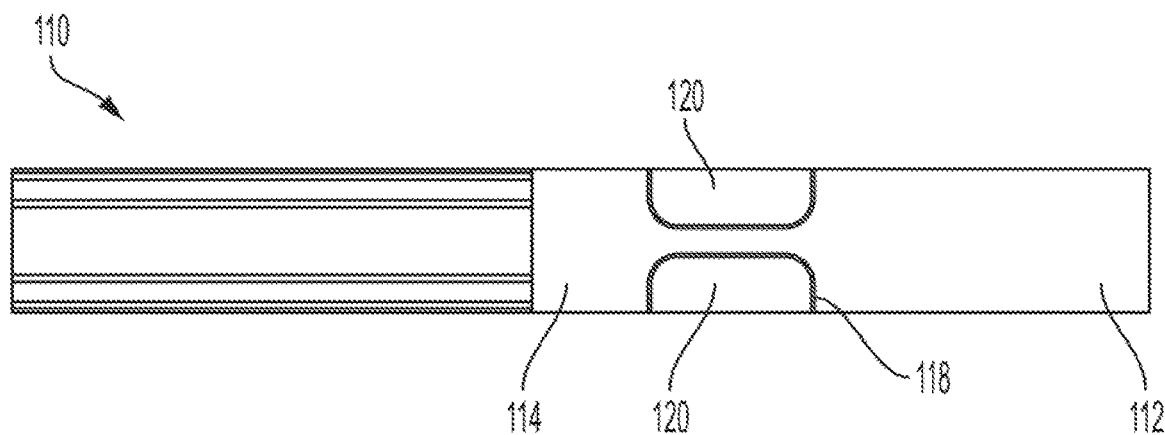
FIGS. 5A and B show the first embodiment of the patient support of the accessory kit, with and without optional filler plates.
Figure 5B:
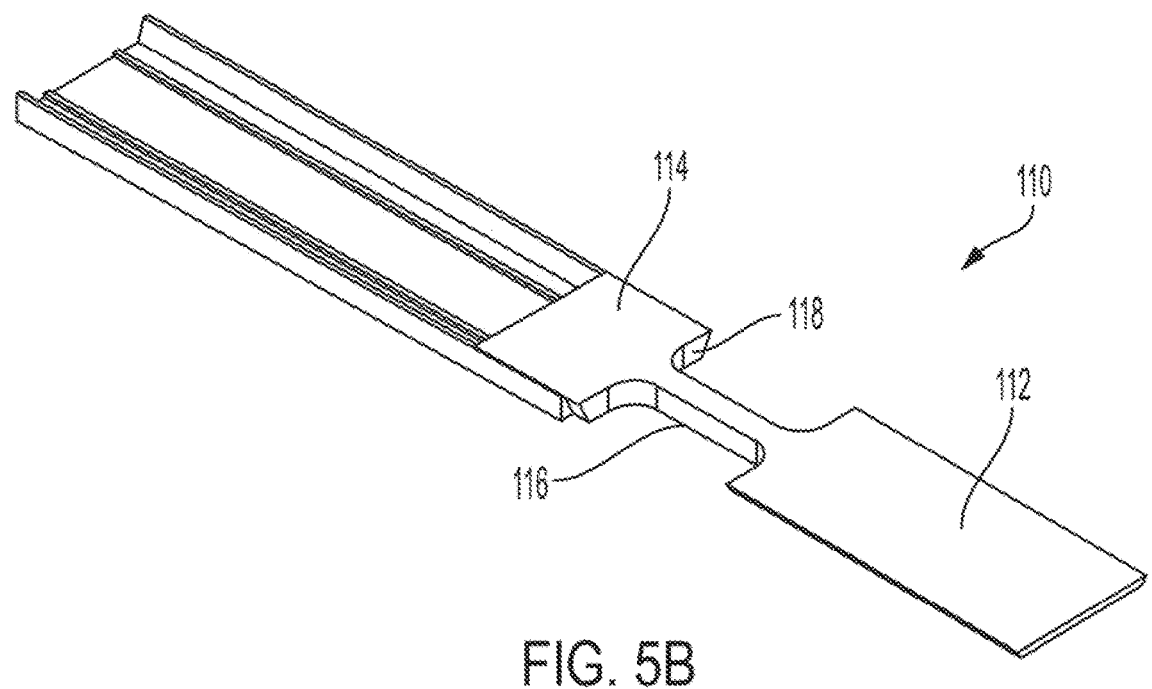
Figure 6A:
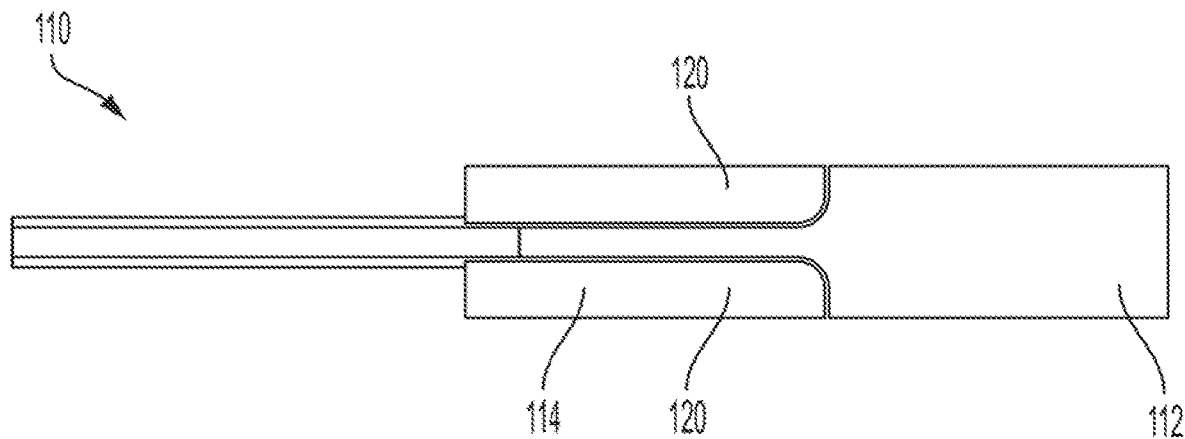
FIGS. 6A and B show the second embodiment of the patient support of the accessory kit, with and without optional filler plates.
Figure 6B:
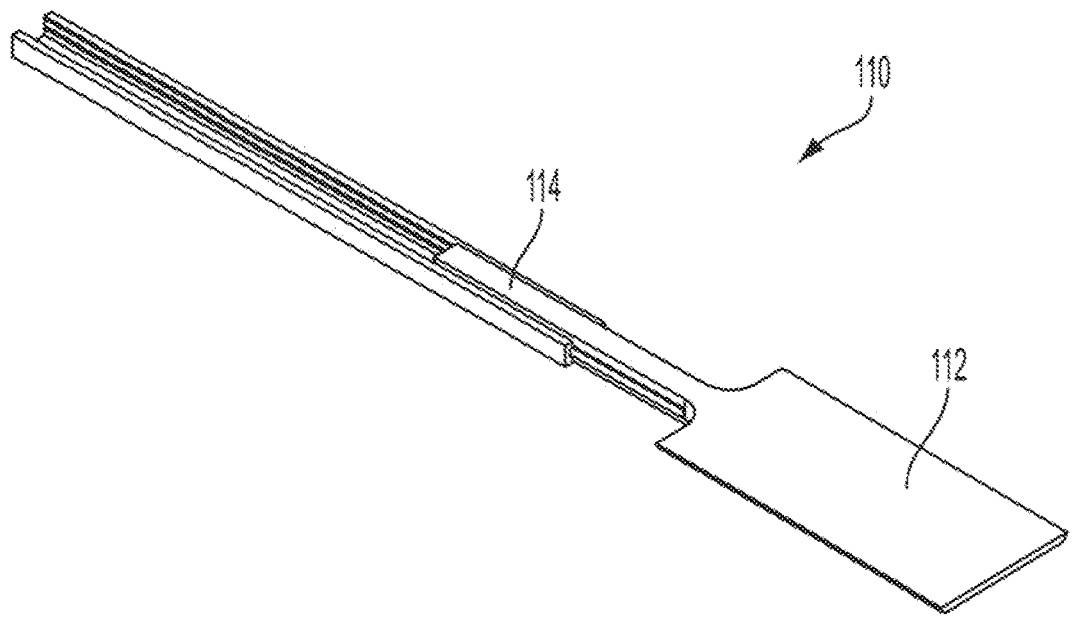

In another embodiment, the patient support 110 may further include a plate or plates 120 that may be optionally used to fill this recess 116 where access is not required, as shown in FIGS. 5A and 6 A.

Figure 4:
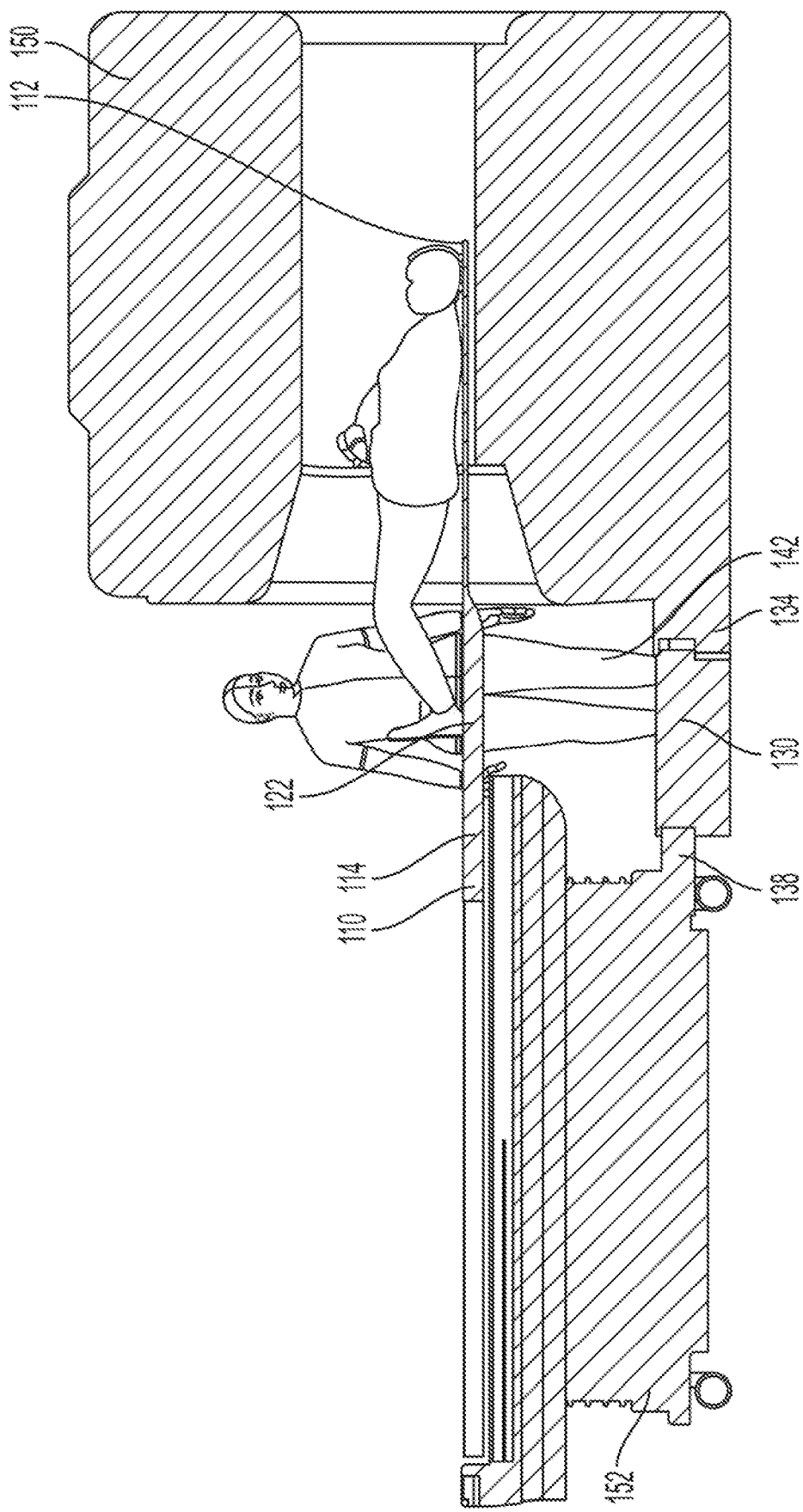
FIG. 4 is a side cross section of an embodiment of the accessory kit installed on an MR scanner and MR scanner table.

In a further preferred embodiment, the patient support 110 includes a structural spine 122 which runs some portion of the length of the patient support, providing additional structural stability. The depth or thickness of the structural spine 122 varies from the proximal end 112 to distal end 114 of the patient support 110, with the depth or thickness of the structural spine 122 having the same depth or thickness as the patient support 110 on the proximal end 112 and gradually becoming larger along the longitudinal axis between the proximal end 112 and distal end 114 of the patient support 110, as shown in FIG. 4. The use of this configuration allows the width of the patient support 110 to be minimized at distal end 114, enabling further enhanced access for the clinician. In a preferred embodiment, the distal end 114 could be narrow on the order of 5 to 10 centimeters in width.

According to another aspect of the invention, an electrical connection adapter 130 is provided for use with an MR scanner 150 and an MR scanner table 152 during interventional procedures using magnetic resonance imaging. The electrical connection adapter 130 includes an external enclosure 140; a proximal connector 132 positioned at a proximal end of the external enclosure 140, the proximal connector 132 being configured to electrically couple the electrical connection adapter 130 to a connector 134 of the MR scanner 150; and a distal connector 136 positioned at a distal end of the external enclosure 140, the distal connector 136 being configured to electrically couple the electrical connection adapter 130 to a connector 138 of the MR scanner table 152. The electrical connection adapter 130 is configured to be interposed between the MR scanner 150 and the MR scanner table 152, thereby creating or extending a gap 142 between the MR scanner 150 and the MR scanner table 152.

Figure 7A:
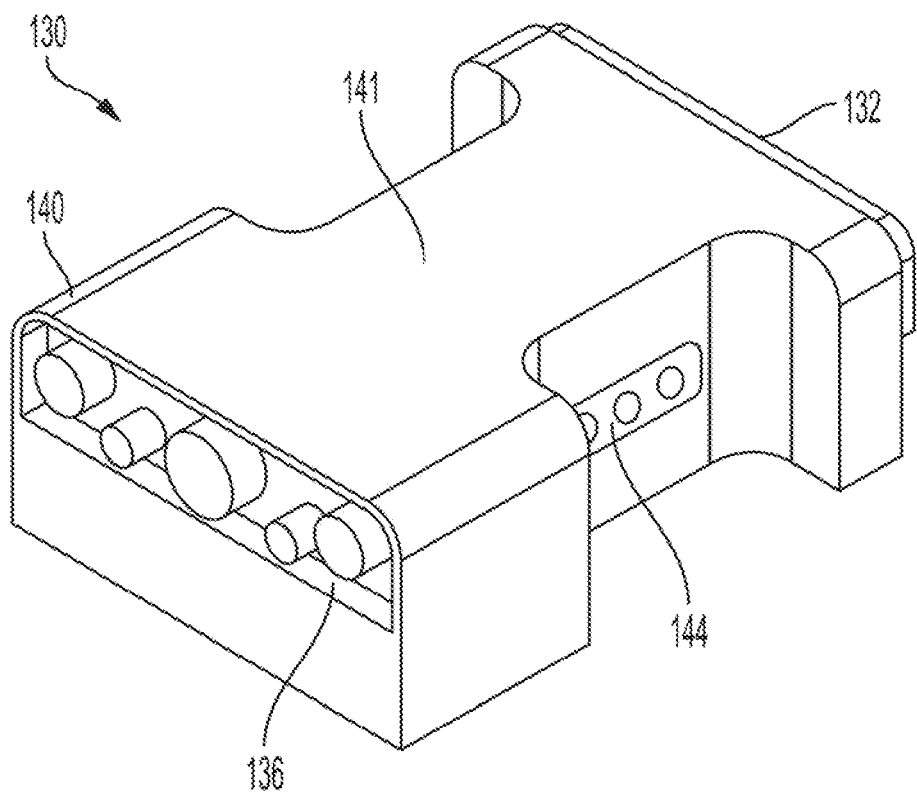
FIGS. 7A and B show an embodiment of the electrical connection adapter of the accessory kit of the present invention.
Figure 7B:
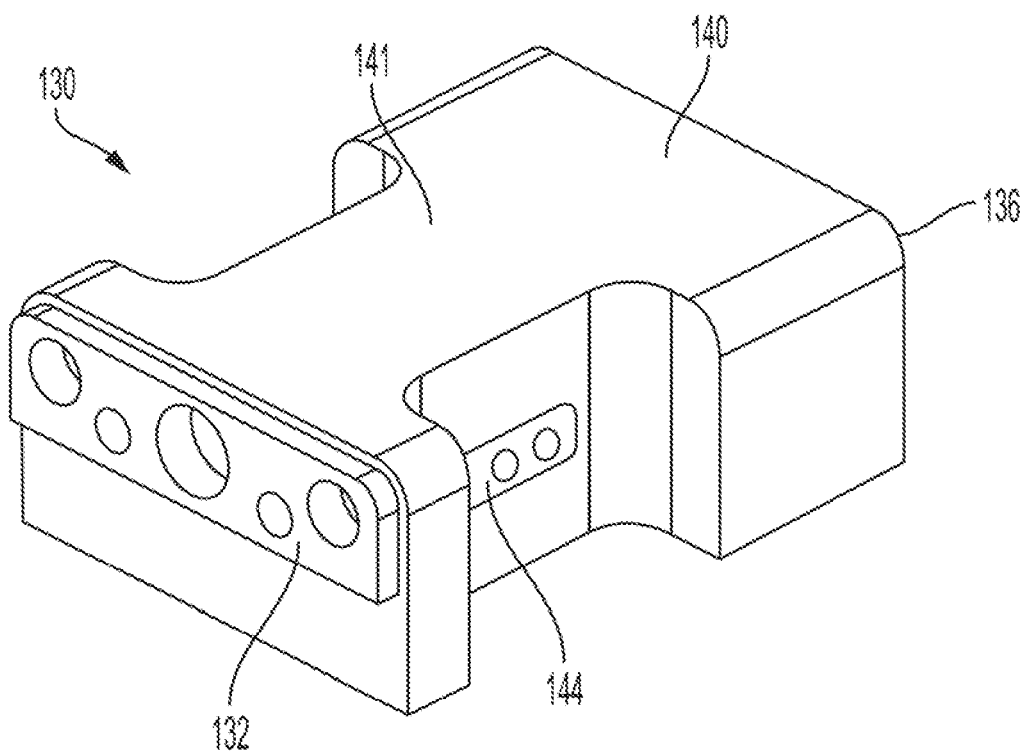

Referring to exemplary embodiments selected to illustrate this aspect of the invention, the electrical connection adapter 130, as shown in FIG. 7, includes a proximal connector 132 located on the end of the electrical connector adapter proximal to the MR scanner. This enables the electrical and mechanical coupling of the electrical connection adapter 130 to a corresponding connector 134 of the compatible MR scanner 150.

Figure 2B:
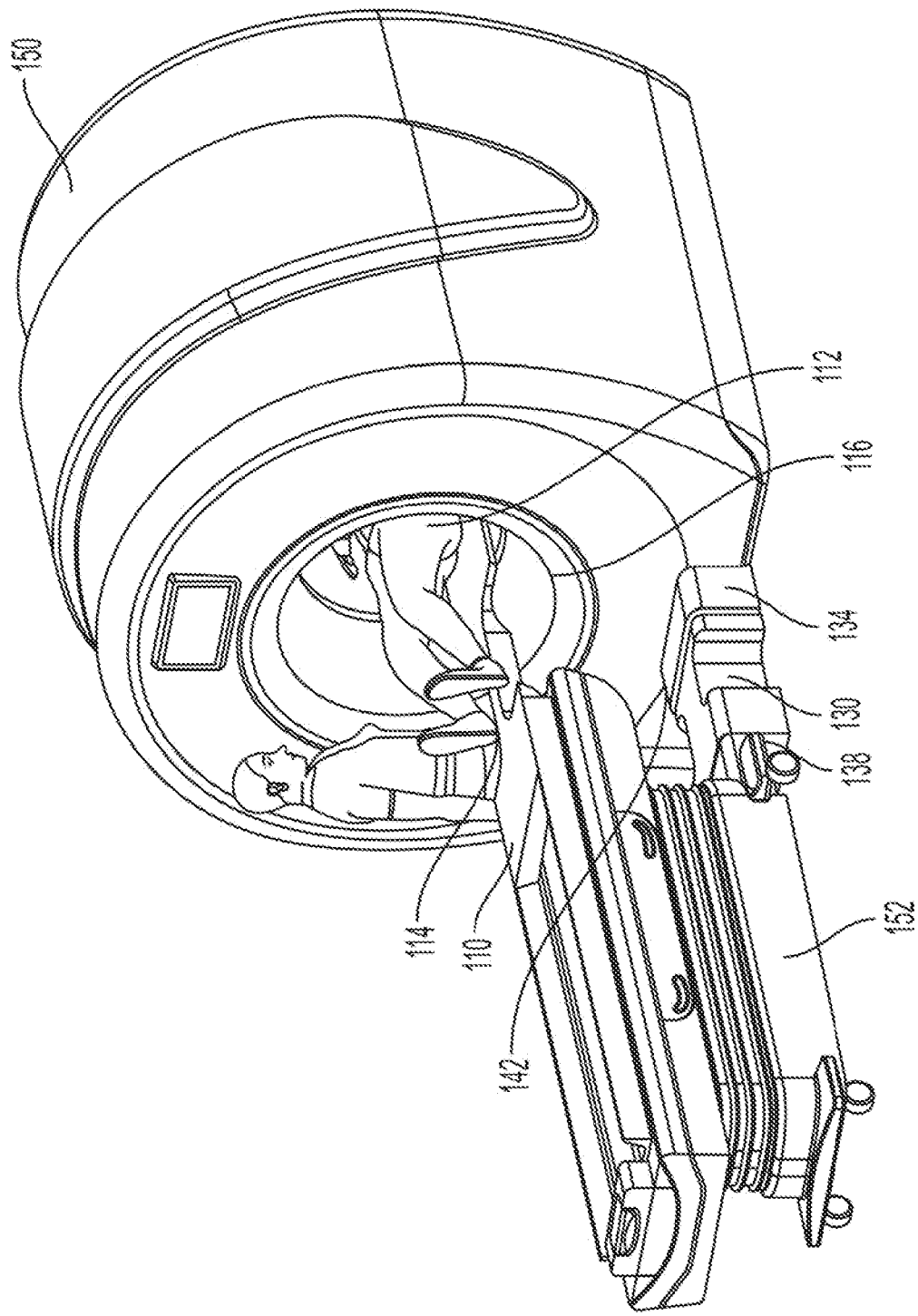

The electrical connection adapter also includes a distal connector 136 enabling the electrical and mechanical coupling of the electrical connection adapter 130 to a corresponding connector 138 of a compatible MR scanner table 152. The electrical connection adapter 130 further comprises an external enclosure 140 which extends the distance between the base of the scanner table 152 and the scanner 150. In this preferred embodiment, shown in FIGS. 2 B, 3 B, and FIG. 4, the electrical connection adapter 130 is configured to act as an extender, connecting the MRI scanner 150 to the MRI table 152, while creating or extending a gap 142 between the two. Accordingly, the electrical connection adapter 130 serves two important functions: it maintains a gap 142 (such as a fixed gap of predetermined size) between the MR scanner table 152 and the MR scanner 150 for access by medical professionals, and it also provides for a reliable electrical connection between the MR scanner 150 and the MR scanner table 152 for the exchange of power and signals.

In a preferred embodiment, the length of gap 142 when the electrical connector adapter 130 is interposed between the MR scanner and MR scanner table is between ¼ meter and 1 meter in length, inclusive, and provides space for the clinician to access the bore. In a further preferred embodiment, the enclosure 140 of the electrical connection adapter 130 is configured such that a clinician may kneel on its top surface 141. In yet another further preferred embodiment, the enclosure 140 of the electrical connection adapter 130 optionally includes additional ergonomic features to aid in clinician comfort. In another embodiment, the electrical connection adapter 130 optionally includes additional ports 144 for power and data outputs, permitting the use of external monitors, image guided interventional tools, and other accessories to enhance the clinician's view of the area of interest and data analysis of the procedure after completion.

When appropriately utilized with a compatible MR scanner 150 and MR scanner table 152, the accessory kit 100 is configured in such a way that, when the proximal end 112 of the patient support 110 is extended into the bore of the MR scanner 150, at least one recess 116 of the distal end 114 of the patient support 110 is exposed outside the bore, extending between the MR scanner and the MR scanner table and longitudinally co-located with the gap 142 created or extended by the electrical connection adapter 130. At this point in operation, the at least one recess 116 of the exposed distal end 114 and the gap 142 between the MR scanner 150 and MR scanner table 152 create at least one recess or access area on one or both sides of the patient support 110 configured to at least partially receive a medical professional, granting the medical professional improved access to the patient during the scan to perform necessary clinical tasks.

Figure 8:
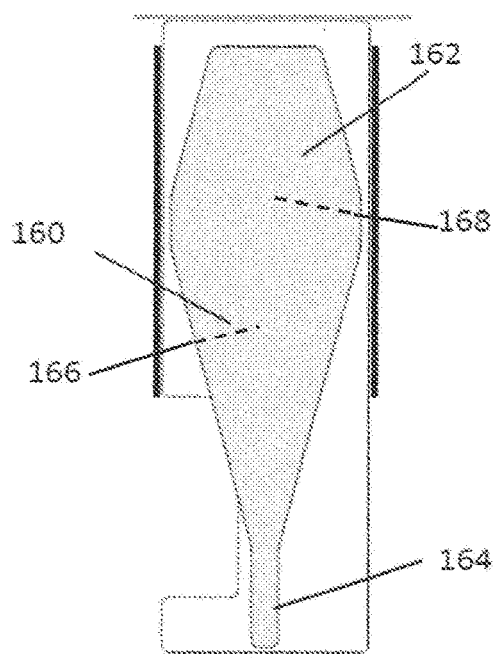
FIG. 8A and B show a further embodiment of the patient support of the accessory kit, with tapered distal end.
Figure 8:
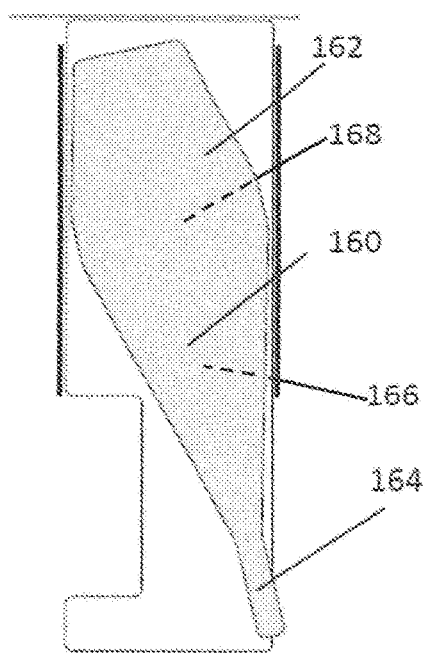

In an alternate embodiment, a secondary support 160 is included for use with the accessory kit 100. The secondary support 160 is removably positioned on top of the patient support 110. The secondary support 160 is tapered from its widest point at the proximal end 162 to a significantly narrowed width at the distal end 164, which then continues at said narrowed width to the termination of the length of the secondary support 160 at the distal end 164, as shown in FIGS. 8A and B. The secondary support 160 is further provided with at least one low friction element, such as an air bearing, wheels, rollers, ball bearings, material surface pairs that result in low friction, or other such low friction element as known to a person having ordinary skill in the art, as well as other equivalent structures as known to a person having ordinary skill in the art. With the low friction element, the secondary support 160 can be moved in multiple directions along the patient support 110, including laterally across the width of patient support 110 and rotatably about an axis perpendicular to the surface of the patient support 110. This rotation and lateral adjustment capability enabled in this embodiment allows fine adjustments in order to provide more optimal access to the patient and better position the target anatomy as close as possible to the isocenter of the MR scanner 150.

In a preferred embodiment, the at least one low friction element is at least one air bearing 166. In a further preferred embodiment, the at least one air bearing 166 further has at least one port 168 configured to introduce air into the at least one air bearing 166. When the at least one air bearing 166 is inflated, the secondary support 160 can be moved in multiple directions along the patient support 110, including laterally across the width of patient support 110 and rotatably about an axis perpendicular to the surface of the patient support 110. This rotation and lateral adjustment capability enabled in this embodiment allows fine adjustments in order to provide more optimal access to the patient and better position the target anatomy as close as possible to the isocenter of the MR scanner 150.

According to another aspect of the invention, an MR imaging system is provided for use during interventional procedures using magnetic resonance imaging. The MR imaging system includes an MR scanner 150; an MR scanner table 152 movable relative to the MR scanner 150; a patient support 110 positioned on the MR scanner table 152, the patient support 110 having a surface extending between a proximal end 112 and a distal end 114, wherein at least one recess 116 is defined in the patient support 110 and extends inwardly from a perimeter of the patient support 110 toward a central region of the patient support 110, the at least one recess 116 being positioned at a distal end portion of the patient support 110 and adapted to at least partially receive a medical professional during interventional procedures. The MR imaging system also includes an electrical connection adapter 130 interposed between the MR scanner 150 and the MR scanner table 152, thereby creating or extending a gap 142 between the MR scanner 150 and the MR scanner table 152. The electrical connection adapter 130 has an external enclosure 140; a proximal connector 132 positioned at a proximal end of the external enclosure, the proximal connector 132 being electrically coupled to a connector 134 of the MR scanner 150. The electrical connection adapter 130 also has a distal connector 136 positioned at a distal end of the external enclosure 140, the distal connector 130 being electrically coupled to a connector 138 of the MR scanner table 152. The patient support 110 on the MR scanner table 152 is movable relative to the MR scanner table 152 towards a bore of the MR scanner 150 and the proximal end 114 of the patient support 110 extends into the bore of the MR scanner 150 such that at least a portion of the at least one recess 116 of the patient support 110 extends into the gap 142 defined between the MR scanner 150 and MR scanner table 152 and is longitudinally co-located with the gap 142 between the MR scanner 150 and MR scanner table 152 created or extended by the electrical connection adapter 130, thereby forming a space to at least partially receive a medical professional for access during the interventional procedures using magnetic resonance imaging. In a separate embodiment, any one of the electrical connection adapter 130 or the patient support 110 may be partially or completely integrally incorporated into the construction of the MR scanner 150. In yet another embodiment, the MR imaging system may incorporate electronic components for interactive interventional radiology, including, among other applications, MR guided ablation using ultrasound, radiofrequency, and/or microwave devices, needle guidance, needle placement, surgical procedures, imaging procedures, pediatric positioning, and imaging aids.

In accordance with yet another aspect of the invention, a method for utilizing the accessory kit 100 (or integrated solution according to a separate embodiment) during clinical interventional procedures is provided. The preferred method includes the following steps:
 a) positioning a patient on a surface of a patient support such that the anatomy of the patient is aligned proximal to the portion of the patient support that will be positioned at an isocenter of the MR scanner (e.g., positioning a patient on a surface of a patient support 110 such that the anatomy of the patient is aligned substantially closely to an isocenter of the MR scanner 150);
 b) extending a proximal end of the patient support into a bore of the MR scanner such that at least a portion of at least one recess defined in the patient support extends between the MR scanner and MR scanner table and is longitudinally co-located with the a gap between the MR scanner and MR scanner table created or extended by an electrical connection adapter previously interposed between the MR scanner and MR scanner table in order to at least partially receive a medical professional (e.g., extending a proximal end 112 of the patient support 110 into a bore of the MR scanner 150 such that at least a portion of the at least one recess 116 of the patient support 110 extends between the MR scanner 150 and MR scanner table 152 and is longitudinally co-located with the gap 142 between the MR scanner 150 and MR scanner table 152 created or extended by an electrical connection adapter 130 previously interposed between the MR scanner 150 and MR scanner table 152 in order to at least partially receive a medical professional); and
 c) receiving at least a portion of a medical professional at least partially within the at least one recess defined by the patient support and the gap created or extended by the electrical connection adapter (e.g., receiving a medical professional at least partially within the at least one recess 116 defined by the patient support 110 and the gap 142 created or extended by the electrical connection adapter 130).

In accordance with still another aspect of the invention, a method for utilizing the accessory kit 100 (or integrated solution in a separate embodiment), a further method for configuring an MR imaging system is also provided. The preferred method includes the following steps:
 a) installing a patient support having a patient surface on an MR scanner table (e.g., installing a patient support 110 having a patient surface on an MR scanner table 150);
 b) engaging a proximal connector of an electrical connection adapter with a connector of the an MR scanner (e.g., engaging a proximal connector 132 of an electrical connection adapter 130 with a connector 134 of the MR scanner 150);
 c) engaging a connector of an MR scanner table with a distal connector of the electrical connection adapter such that the electrical connection adapter is interposed between the MR scanner and MR scanner table, thereby creating or extending a gap between the MR scanner and the MR scanner table (e.g., engaging a connector 138 of an MR scanner table 152 with a distal connector 136 of the electrical connection adapter 130 such that the electrical connection adapter 130 is interposed between the MR scanner 150 and MR scanner table 152, thereby creating or extending a gap between the MR scanner 150 and MR table 152); and
 d) extending a proximal end of the patient support into a bore of the MR scanner such that the proximal end of the patient support extends into the bore of the MR scanner, at least a portion of the at least one recess of the patient support extends to a location corresponding to the gap between the MR scanner and the MR scanner table, and the at least one recess is longitudinally co-located with the gap between the MR scanner and the MR scanner table created or extended by the electrical connection adapter in order to at least partially receive a medical professional (e.g., extending a proximal end 112 of the patient support 110 into a bore of the MR scanner 150 such that that the proximal end 112 of the patient support 110 extends into the bore of the MR scanner 150 such that at least a portion of the at least one recess 116 of the patient support 110 extends between the MR scanner 150 and MR scanner table 152 and is longitudinally co-located with the gap 142 between the MR scanner 150 and MR scanner table 152 created or extended by the electrical connection adapter 130 in order to at least partially receive a medical professional).

Various non-limiting aspects of the invention are summarized below.

Aspect 1. An MR imaging system configured for use during interventional procedures using magnetic resonance imaging, the MR imaging system comprising:
 an MR scanner;
 an MR scanner table movable relative to the MR scanner;

a patient support positioned on the MR scanner table, the patient support having a surface extending between a proximal end and a distal end, wherein at least one recess is defined in the patient support and extends inwardly from a perimeter of the patient support toward a central region of the patient support, the at least one recess being positioned at a distal end portion of the patient support and adapted to at least partially receive a medical professional during interventional procedures;

an electrical connection adapter interposed between the MR scanner and the MR scanner table, thereby creating or extending a gap between the MR scanner and the MR scanner table, the electrical connection adapter having:

an external enclosure;

a proximal connector positioned at a proximal end of the external enclosure, the proximal connector being electrically coupled to a connector of the MR scanner; and a distal connector positioned at a distal end of the external enclosure, the distal connector being electrically coupled to a connector of the MR scanner table;

wherein the patient support on the MR scanner table is movable relative to the MR scanner table towards a bore of the MR scanner and the proximal end of the patient support extends into the bore of the MR scanner such that at least a portion of the at least one recess of the patient support extends into the gap defined between the MR scanner and MR scanner table and is longitudinally co-located with the gap between the MR scanner and MR scanner table created or extended by the electrical connection adapter, thereby forming a space to at least partially receive a medical professional for access during the interventional procedures using magnetic resonance imaging.

Aspect 2. The MR imaging system of Aspect 1, wherein the at least one recess of the patient support comprises at least one cutout in at least one side of the patient support.

Aspect 3. The MR imaging system of either Aspect 1 or 2, wherein the patient support further comprises a structural spine, wherein the structural spine runs at least a portion of the length of the device and has a thickness no less than the thickness of a proximal end portion of the patient support at the proximal end of the patient support.

Aspect 4. The MR imaging system of Aspect 3, wherein the thickness of the structural spine increases in a longitudinal direction extending from the proximal end of the patient support to the distal end.

Aspect 5. The MR imaging system of any of Aspects 1-4, wherein the at least one recess extends to the distal end of the patient support such that a width of the patient support at the distal end is narrower than a width of the patient support at the proximal end.

Aspect 6. The MR imaging system of any of Aspects 1-5, wherein the width of the distal end of the patient support is no greater than 10 cm.

Aspect 7. The MR imaging system of any of Aspects 1-6, wherein the patient support replaces a surface of a conventional MR scanner table.

Aspect 8. The MR imaging system of any of Aspects 1-7, wherein the patient support further comprises at least one filler plate positionable to fill in the at least one recess.

Aspect 9. The MR imaging system of any of Aspects 1-8, wherein the patient support is made only of materials which are compatible with magnetic resonance imaging environments.

Aspect 10. The MR imaging system of Aspect 9, wherein the patient support is composed of non-ferromagnetic, non-conducting, and non-metallic composite materials.

Aspect 11. The MR imaging system of any of Aspects 1-10, wherein the patient support further comprises indicia configured to aid in alignment of a region of interest to an isocenter of the MR scanner.

Aspect 12. The MR imaging system of any of Aspects 1-11, wherein the length of the gap created or extended by the electrical connection adapter is between ¼ m and 1 m.

Aspect 13. The MR imaging system of any of Aspects 1-12, wherein the electrical connection adapter further comprises additional ports for supplemental power and data output.

Aspect 14. The MR imaging system of any of Aspects 1-13, wherein the enclosure of the electrical connection adapter is configured and positionable to permit a medical professional to kneel on it.

Aspect 15. The MR imaging system of Aspect 14, wherein the enclosure of the electrical connection adapter further comprises ergonomic surfaces configured for enhancing comfort of the medical professional.

Aspect 16. The MR imaging system of any of Aspects 1-15, wherein any of the components are at least partially integrated into the construction of the MR scanner.

Aspect 17. The MR imaging system of any of Aspects 1-16, wherein the MR imaging system further comprises components for interactive interventional radiology.

Aspect 18. An accessory kit for use with an MR scanner and an MR scanner table during interventional procedures using magnetic resonance imaging, the accessory kit comprising:

a patient support configured to be positioned on the MR scanner table and having a surface extending between a proximal end and a distal end, wherein at least one recess is defined in the patient support and extends inwardly from a perimeter of the patient support toward a central region of the patient support, the at least one recess being positioned at a distal end portion of the patient support and adapted to at least partially receive a medical professional during interventional procedures;

and an electrical connection adapter configured to be interposed between the MR scanner and the MR scanner table, thereby creating or extending a gap between the MR scanner and the MR scanner table when the electrical connection adapter is interposed between the MR scanner and the MR scanner table, the electrical connection adapter having:

an external enclosure;

a proximal connector positioned at a proximal end of the external enclosure, the proximal connector being configured to electrically couple the electrical connection adapter to a connector of the MR scanner; and a distal connector positioned at a distal end of the external enclosure, the distal connector being configured to electrically couple the electrical connection adapter to a connector of the MR scanner table.

Aspect 19. The accessory kit of Aspect 18, wherein the at least one recess comprises at least one cutout in at least one side of the patient support.

Aspect 20. The accessory kit of either Aspect 18 or 19, wherein the patient support further comprises a structural spine, wherein the structural spine runs at least a portion of the length of the patient support and has a thickness no less than the thickness of a proximal end portion of the patient support at the proximal end of the patient support.

Aspect 21. The accessory kit of Aspect 20, wherein the thickness of the structural spine increases in a longitudinal direction extending from the proximal end to the distal end of the patient support.

Aspect 22. The accessory kit of any of Aspects 18-20, wherein the at least one recess extends to the distal end of the patient support such that a width of the patient support at the distal end is narrower than a width of the patient support at the proximal end.

Aspect 23. The accessory kit of any of Aspects 18-22, wherein the width of the distal end of the patient support is no greater than 10 cm.

Aspect 24. The accessory kit of any of Aspects 18-23, wherein the patient support replaces a surface of a conventional MR scanner table.

Aspect 25. The accessory kit of any of Aspects 18-23, wherein the patient support further comprises at least one filler plate positionable to fill in the at least one recess.

Aspect 26. The accessory kit of any of Aspects 18-24, wherein the patient support is composed only of materials which are compatible with magnetic resonance imaging environments.

Aspect 27. The accessory kit of Aspect 26, wherein the patient support is composed of non-ferromagnetic, non-conducting, and non-metallic composite materials.

Aspect 28. The accessory kit of any of Aspects 16-27, wherein the patient support further comprises indicia configured to aid in alignment of a region of interest to an isocenter of the MR scanner.

Aspect 29. The accessory kit of any of Aspects 16-27, wherein the length of the gap created or extended by the electrical connection adapter is between ¼ m and 1 m.

Aspect 30. The accessory kit of any of Aspects 16-27, wherein the electrical connection adapter further comprises additional ports for supplemental power and data output.

Aspect 31. The accessory kit of any of Aspects 16-30, wherein the enclosure of the electrical connection adapter is configured and positionable to permit a medical professional to kneel on it.

Aspect 32. The accessory kit of Aspect 31, wherein the enclosure of the electrical connection adapter further comprises ergonomic surfaces configured for enhancing comfort of the medical professional.

Aspect 33. The accessory kit of any of any of Aspects 16-32, wherein the gap created or extended by the electrical connection adapter and the at least one recess are longitudinally co-located when the patient support is positioned on the MR scanner table, the electrical connection adapter is interposed between the MR scanner and the MR scanner table, and the patient support is moved relative to the MR scanner table towards a bore of the MR scanner and the proximal end of the patient support extends into the bore of the MR scanner.

Aspect 34. The accessory kit of Aspect 18 wherein the accessory kit further comprises at least one secondary support which may be movably positioned on the patient support.

Aspect 35. The accessory kit of Aspect 34 wherein the secondary support is tapered from its widest point at the proximal end to a significantly narrowed width at the distal end, which then continues at said narrowed width to the termination of the length of the patient support at the distal end.

Aspect 36. The accessory kit of Aspect 34 wherein the secondary support additionally comprises at least one air bearing and at least one port configured to introduce air into the at least one air bearing.

Aspect 37. The accessory kit of Aspect 34 wherein the secondary support is configured to be movably positioned on the surface of the patient support, including laterally across the width of the patient support and rotatably about an axis perpendicular to the surface of the patient support.

Aspect 38. An electrical connection adapter for use with an MR scanner and an MR scanner table during interventional procedures using magnetic resonance imaging, the electrical connection adapter comprising:
    an external enclosure;
    a proximal connector positioned at a proximal end of the external enclosure, the proximal connector being configured to electrically couple the electrical connection adapter to a connector of the MR scanner; and
    a distal connector positioned at a distal end of the external enclosure, the distal connector being configured to electrically couple the electrical connection adapter to a connector of the MR scanner table;
    wherein the electrical connection adapter is configured to be interposed between the MR scanner and the MR scanner table, thereby creating or extending a gap between the MR scanner and the MR scanner table.

Aspect 39. The electrical connection adapter of Aspect 38, wherein the length of the electrical connection adapter is configured to maintain the gap created or extended by the electrical connection adapter between ¼ m and 1 m, the electrical connector adapter having a length of at least ¼ m and 1 m.

Aspect 40. The electrical connection adapter of either Aspect 38 or 39, wherein the electrical connection adapter further comprises additional ports for supplemental power and data output.

Aspect 41. The electrical connection adapter of any of Aspects 38-40, wherein the enclosure of the electrical connection adapter is configured and positionable to permit a medical professional to kneel on it.

Aspect 42. The electrical connection adapter of any of Aspects 38-41, wherein the enclosure of the electrical connection adapter further comprises ergonomic surfaces configured for enhancing comfort of the medical professional.

Aspect 43. A method of using an MR scanner and an MR scanner table for interventional procedures using magnetic resonance imaging, the method comprising:
    positioning a patient on a surface of a patient support such that the anatomy of the patient is aligned proximal to the portion of the patient support that will be positioned at an isocenter of the MR scanner;
    extending a proximal end of the patient support into a bore of the MR scanner such that at least a portion of at least one recess defined in the patient support extends between the MR scanner and MR scanner table and is longitudinally co-located with the a gap between the MR scanner and MR scanner table created or extended by an electrical connection adapter previously interposed between the MR scanner and MR scanner table in order to at least partially receive a medical professional; and
    receiving at least a portion of a medical professional at least partially within the at least one recess defined by the patient support and the gap created or extended by the electrical connection adapter.

Aspect 44. The method of Aspect 43 further comprising the following steps:

Placing a secondary support having at least one low friction element.

Adjusting the lateral position of the secondary support and rotational position of the secondary support in an axis perpendicular to the surface of the patient support such that the anatomy of the patient is positioned at isocenter of the MR scanner.

Aspect 45. A method of configuring an MR imaging system for access during interventional procedures using magnetic resonance imaging, the method comprising:

installing a patient support having a patient surface on an MR scanner table;

engaging a proximal connector of an electrical connection adapter with a connector of an MR scanner;

engaging a connector of an MR scanner table with a distal connector of the electrical connection adapter such that the electrical connection adapter is interposed between the MR scanner and MR scanner table, thereby creating or extending a gap between the MR scanner and the MR scanner table; and extending a proximal end of the patient support into a bore of the MR scanner such that the proximal end of the patient support extends into the bore of the MR scanner, at least a portion of the at least one recess of the patient support extends to a location corresponding to the gap between the MR scanner and the MR scanner table, and the at least one recess is longitudinally co-located with the gap between the MR scanner and the MR scanner table created or extended by the electrical connection adapter in order to at least partially receive a medical professional.

Aspect 46. The method of Aspect 45 further comprising the following step:

placing a secondary support having an air bearing and port to introduce air into the at least one air bearing on the patient support.

Aspect 47. A patient support for use with an MR scanner and an MR scanner table during interventional procedures using magnetic resonance imaging, the patient support having a surface extending between a proximal end and a distal end, wherein at least one recess extends inwardly from a perimeter of the patient support toward a central region of the patient support, the at least one recess being positioned substantially at the distal end of the patient support and adapted to at least partially receive a medical professional during interventional procedures, wherein the patient support is configured to be movable into the bore of the MR scanner so that the distal end of the patient support extends beyond a proximal end of the MR scanner table and at least a portion of the at least one recess is exposed to at least partially receive a medical professional.

Aspect 48. The patient support of Aspect 47, wherein the at least one recess comprises at least one cutout in at least one side of the patient support.

Aspect 49. The patient support of either Aspect 47 or 48, wherein the patient support further comprises a structural spine, wherein the structural spine runs a portion of the length of the patient support and has a depth no less than the depth of the proximal end of the patient support at the proximal end of the patient support.

Aspect 50. The patient support of any of Aspects 47-49, wherein the depth of structural spine increases in a longitudinal direction extending from the proximal end to the distal end.

Aspect 51. The patient support of Aspect 50, wherein the at least one recess comprises a distal end of the patient support with a width substantially narrower than the width of the proximal end.

Aspect 52. The patient support of Aspect 51, wherein the width of the distal end of the patient support is no greater than 10 cm.

Aspect 53. The patient support of any of Aspects 47-52, wherein the patient support replaces the existing surface of the MR scanner table.

Aspect 54. The patient support of any of Aspects 47-53, wherein the patient support further comprises at least one filler plate which fills in the at least one recess.

Aspect 55. The patient support of any of Aspects 47-54, wherein the patient support is made only of materials which are compatible with magnetic resonance imaging environments.

Aspect 56. The patient support of Aspect 55, wherein the patient support is composed of non-ferromagnetic, non-conducting, non-metallic composite materials.

Aspect 57. The patient support of any of Aspects 47-56, wherein the patient support further comprises crosshairs or other markings configured to aid in alignment of a region of interest to the isocenter of the scanner.

Aspect 58. A secondary support configured for use with a patient support, the secondary support having a proximal end, a distal end, side edges extending between the proximal end and the distal end, and a width extending between the side edges, the width of the secondary support varying between the proximal end and the distal end such that the width at a proximal end portion is greater than the width at a distal end portion, wherein the secondary support is configured for movement relative to the patient support such that is can be movably positioned on a top surface of the patient support.

Aspect 59. The secondary support of Aspect 58 wherein the secondary support is tapered from its widest point at the proximal end to a significantly narrowed width at the distal end, which then continues at said narrowed width to the termination of the length of the secondary support at the distal end.

Aspect 60. The secondary support of either Aspect 58 or 59 wherein the secondary support further comprises at least one low friction element.

Aspect 61. The secondary support of Aspect 60 wherein the low friction element is at least one air bearing and further comprises at least one port configured to introduce air into the at least one air bearing.

Aspect 62. The secondary support of any of Aspects 58-61 wherein the secondary support is configured to be movably positioned on the surface of the patient support, including laterally across the width of the patient support and rotatably about an axis perpendicular to the surface of the patient support.

What is claimed is:

1. An electrical connection adapter and patient support system for use with an MR scanner and an MR scanner table during interventional procedures using magnetic resonance imaging, the electrical connection adapter and patient support system comprising:

a patient support configured to be positioned on the MR scanner table; and an electrical connection adapter comprising:

an external enclosure;
a proximal connector positioned at a proximal end of the external enclosure, the proximal connector being configured to electrically couple the electrical connection adapter to a connector of the MR scanner; and
a distal connector positioned at a distal end of the external enclosure, the distal connector being configured to electrically couple the electrical connection adapter to a connector of the MR scanner table;
wherein the electrical connection adapter is configured to be interposed between the MR scanner and the MR scanner table, thereby creating or extending a gap between the MR scanner and the MR scanner table;
wherein the patient support has a surface extending between the proximal end and a distal end of the patient support; and
wherein at least one recess is defined in at least one side of the patient support and extends inwardly from a perimeter of the patient support toward a central region of the patient support, the at least one recess being positioned at a distal end portion of the patient support and is adapted to extend into the gap between the MR scanner and MR scanner table when created or extended by the electrical connection adapter, and is longitudinally co-located with the gap between the MR scanner and MR scanner table when created or extended by the electrical connection adapter, thereby forming a space configured to at least partially receive a medical professional for access during the interventional procedures using magnetic resonance imaging.

2. The electrical connection adapter and patient support system of claim 1, wherein the electrical connection adapter further comprises additional ports for supplemental power and data output.

3. An MR imaging system configured for use during interventional procedures using magnetic resonance imaging, the MR imaging system comprising:
an MR scanner;
an MR scanner table movable relative to the MR scanner; and
the electrical connection adapter and patient support system of claim 1, the electrical connection adapter being interposed between the MR scanner and the MR scanner table, thereby creating or extending the gap between the MR scanner and the MR scanner table, and the distal connector of the electrical connection adapter being electrically coupled to a connector of the MR scanner table;
wherein the patient support is positioned on the MR scanner table and is movable relative to the MR scanner table towards a bore of the MR scanner and a proximal end of the patient support extends into the bore of the MR scanner and extends into the gap defined between the MR scanner and MR scanner table created or extended by the electrical connection adapter.

4. The MR imaging system of claim 3, wherein the at least one recess extends to the distal end of the patient support such that a width of the patient support at the distal end of the patient support is narrower than a width of the patient support at the proximal end of the patient support.

5. The MR imaging system of claim 3, wherein the patient support replaces the existing surface of the MR scanner table.

6. The MR imaging system of claim 3, wherein the patient support further comprises at least one filler plate positionable to fill in the at least one recess.

7. The MR imaging system of claim 3, wherein at least one of the electrical connection adapter or the patient support is at least partially integrated into the construction of the MR scanner.

8. The MR imaging system of claim 3, wherein the MR imaging system further comprises components for interactive interventional radiology.

9. The MR imaging system of claim 3, further comprising:
a secondary support configured for use with the patient support, wherein the secondary Support further comprises at least one low friction element.

10. The MR imaging system of claim 9, wherein said low friction element comprises at least one air bearing further having at least one port configured to introduce air into the at least one air bearing.

11. The MR imaging system of claim 9, wherein the secondary support is configured to be movably positioned on the surface of the patient support, including moving laterally across a width of the patient support and moving rotatably about an axis perpendicular to the surface of the patient support.

12. A method of configuring an MR imaging system for access during interventional procedures using magnetic resonance imaging, the method comprising:
installing a patient support having a patient surface on an MR scanner table;
engaging a proximal connector of an electrical connection adapter with a connector of an MR scanner;
engaging a connector of the MR scanner table with a distal connector of the electrical connection adapter such that the electrical connection adapter is interposed between the MR scanner and the MR scanner table, thereby creating or extending a gap between the MR scanner and the MR scanner table; and
extending a proximal end of the patient support into a bore of the MR scanner such that the proximal end of the patient support extends into the bore of the MR scanner, at least a portion of at least one recess of the patient support extends to a location corresponding to the gap between the MR scanner and the MR scanner table, and the at least one recess of the patient support is longitudinally co-located with the gap between the MR scanner and the MR scanner table created or extended by the electrical connection adapter in order to at least partially receive a medical professional.

13. The method of claim 12, further comprising the step:
placing a secondary support having an air bearing and port to introduce air into the at least one air bearing on the secondary support.

* * * * *